United States Patent [19]

Errico et al.

[11] Patent Number: 5,785,711

[45] Date of Patent: Jul. 28, 1998

[54] POLYAXIAL PEDICLE SCREW HAVING A THROUGH BAR CLAMP LOCKING MECHANISM

[75] Inventors: Joseph P. Errico, Far Hills; Thomas J. Errico, Summit; James D. Ralph, Oakland; Stephen Tatar, Montville, all of N.J.

[73] Assignee: Third Millennium Engineering, LLC, Summit, N.J.

[21] Appl. No.: 856,773

[22] Filed: May 15, 1997

[51] Int. Cl.⁶ .................................................. A61B 17/70
[52] U.S. Cl. ................................. 606/61; 606/60; 606/73
[58] Field of Search ............................... 606/60, 61, 69, 606/70, 71, 72, 73, 104; 623/16, 17

[56] References Cited

U.S. PATENT DOCUMENTS

| 4,946,458 | 8/1990 | Harms et al. | 606/61 |
|---|---|---|---|
| 5,122,131 | 6/1992 | Tsou | 606/61 |
| 5,261,909 | 11/1993 | Sutterlin et al. | 606/61 |
| 5,344,422 | 9/1994 | Frigg | 606/61 |
| 5,549,608 | 8/1996 | Errico et al. | 606/61 |
| 5,645,544 | 7/1997 | Tai et al. | 606/61 |
| 5,683,392 | 11/1997 | Richelsoph et al. | 606/61 |

*Primary Examiner*—Michael Buiz
*Assistant Examiner*—David O. Reip
*Attorney, Agent, or Firm*—Joseph P. Errico, Esq.

[57] ABSTRACT

A polyaxial orthopedic device for use with rod implant apparatus includes a screw having a curvate head, a cross bar mounting element having a socket into which the head of the screw is initially polyaxially nested. The cross bar mounting element further includes a vertical split which permits the socket to be expanded or compressed via the application of a corresponding force directed at the split. The cross bar mounting element further includes a pair of upwardly extending members which define a trough into which a cross bar element is positioned. The cross bar element includes features which permit the secure fixation of a rod thereto, as well as a selectively slideable element, such as a nut, which may be tightened to apply the compressive force necessary to compress the interior volume onto the head of the screw, thus locking the assembly in place.

11 Claims, 6 Drawing Sheets

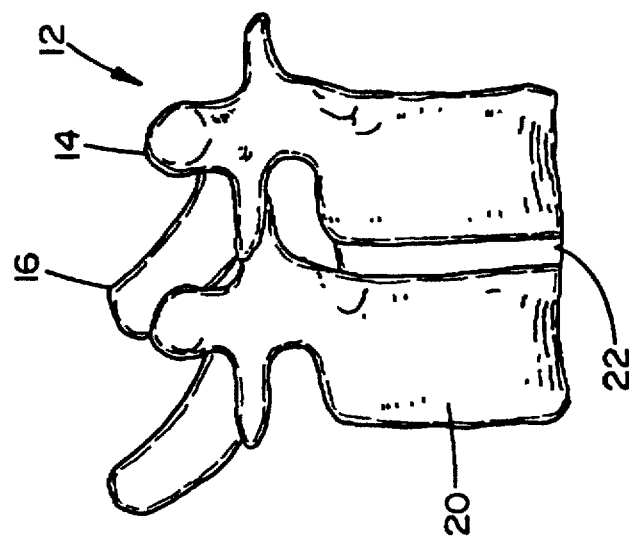
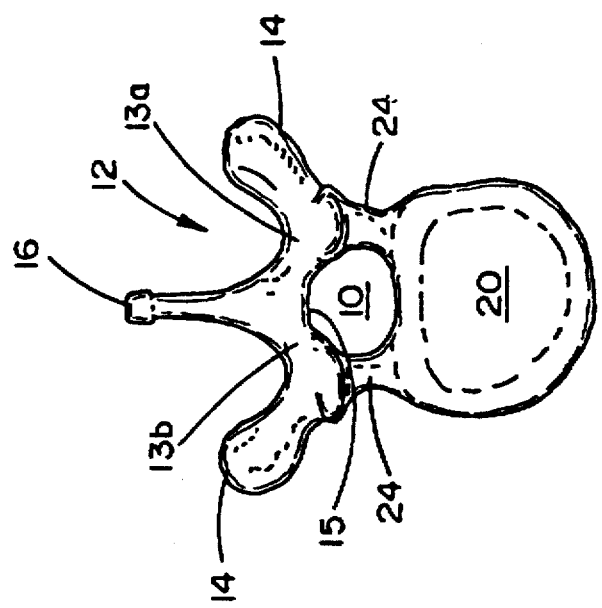

POLYAXIAL PEDICLE SCREW HAVING A THROUGH BAR CLAMP LOCKING MECHANISM

BACKGROUND OF THE INVENTION

1. Field of the Invention

This invention relates generally to a polyaxial pedicle screw and, more particularly, to a screw for insertion into spinal bone having a polyaxial coupling and locking mechanism for mounting a stabilizing rod to a sequence of vertebrae.

2. Description of the Prior Art

The bones and connective tissue of an adult human spinal column consists of more than 20 discrete bones coupled sequentially to one another by a tri-joint complex which consist of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic and lumbar spine. For the purposes of this disclosure, however, the word spine shall refer only to the cervical region.

Referring now to FIGS. 1, 2, and 3, top, side, and posterior views of a vertebral body, a pair of adjacent vertebral bodies, and a sequence of vertebral bodies are shown, respectively. The spinal cord is housed in the central canal 10, protected from the posterior side by a shell of bone called the lamina 12. The lamina 12 includes a rearwardly and downwardly extending portion called the spinous process 16, and laterally extending structures which are referred to as the transverse processes 14. The anterior portion of the spine comprises a set of generally cylindrically shaped bones which are stacked one on top of the other. These portions of the vertebrae are referred to as the vertebral bodies 20, and are each separated from the other by the intervertebral discs 22. The pedicles 24 comprise bone bridges which couple the anterior vertebral body 20 to the corresponding lamina 12.

The spinal column of bones is highly complex in that it includes over twenty bones coupled to one another, housing and protecting critical elements of the nervous system having innumerable peripheral nerves and circulatory bodies in close proximity. In spite of these complexities, the spine is a highly flexible structure, capable of a high degree of curvature and twist in nearly every direction. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classifications suggest, lateral and anterior assemblies are coupled to the anterior portion of the spine, which is the sequence of vertebral bodies. Posterior implants generally comprise pairs of rods, which are aligned along the axis which the bones are to be disposed, and which are then attached to the spinal column by either hooks which couple to the lamina or attach to the transverse processes, or by screws which are inserted through the pedicles.

"Rod assemblies" generally comprise a plurality of such screws which are implanted through the posterior lateral surfaces of the laminae, through the pedicles, and into their respective vertebral bodies. The screws are provided with upper portions which comprise, or have mounted thereto, coupling elements for receiving and securing an elongate rod therethrough. The rod extends along the axis of the spine, coupling to the plurality of screws via their coupling elements. The rigidity of the rod may be utilized to align the spine in conformance with a more desired shape.

It has been identified, however, that a considerable difficulty is associated with inserting screws along a misaligned curvature and simultaneously exactly positioning the coupling elements such that the rod receiving portions thereof are aligned so that the rod can be passed therethrough without distorting the screws. Attempts at achieving proper alignment with fixed screws is understood to require increased operating time, which is known to enhance many complications associated with surgery. Often surgical efforts with such fixed axes devices cannot be achieved, thereby rendering such instrumentation attempts entirely unsucessful.

The art contains a variety of attempts at providing instrumentation which permit a limited freedom with respect to angulation of the screw and the coupling element. These teachings, however, are generally complex, inadequately reliable, and lack long-term durability. These considerable drawbacks associated with prior art systems also include difficulty properly positioned the rod and coupling elements, and the tedious manipulation of the many small parts in the operative environment.

One such inferior solution is provided in the TSRH™ spine system, produced by Sofamor Danek™. This product, illustrated in FIGS. 4a and 4b, comprises a fixed-axis screw 40 having a threaded shaft 42 and a pair of upwardly extending members 46a,46b which define a U-shaped upper portion 45. The front and back faces 46a,46b (back faces not shown) of the upwardly extending members 46a,46b are splined with a radially extending ridges 48.

Referring now to FIG. 4b also, a fixed cross bar member 50, which is mounted in the trough of the U-shaped upper portion 45 and transverse to the overall axis of the screw 40, is shown. The cross bar member 50 includes a first end 52 which is threaded, onto which a nut 54 may be advanced. The second end 56 of the cross bar member 50 comprises a hole 58 through which a rod may be disposed. The diameter of the first end 52 is less than the diameter of the second end 56. An annular member 60 is slideably mounted about the middle of the cross-bar member (at the junction of the first and second ends) which has opposing faces 62 and 64. The first face 62, which addresses the first end 52, has a splined conformation, such that it may join with the splined faces 46a,46b of the U-shaped section of the screw 40 (the splining permits a rotational variety of interfacing angles). The second face 64 includes a groove 66 in which the rod may nest when it is positioned through the hole 58. When the first end 42 of the cross bar member 50 is positioned in the U-shaped trough, and the nut 54 is advanced, the first face of the disc 60 locks to the splined faces 46a, 46b of the screw 40, by virtue of the mutual splines. The annulus 60 itself is then slideably pushed toward the second end 56 of the cross-bar member 50 until the second face 64 of the annulus, and more particularly the groove 66, compresses the rod in the hole 58 of the cross bar member 50. This tightening of the nut 54, therefore, locks the assembly together.

The TSRH™ spine system requires a multitude of cross bar lengths to account for different anatomies, which control the distance of the rod from the screw head. In addition, the fixed nature of the head of the screw severely limits the freedom of the surgeon to angulate the screws and to rotate the cross bar relative to the shaft portion. (The cross bar can only be rotated into a limited number of positions-all of which are transverse to the head of the screw. In a fixed axis screw system, this means the cross bar is always transverse to the shaft.) This limitation requires that screws be left higher—more "proud"—than would otherwise be comfortable for the post operative patient.

It is, therefore, the principal object of the present invention to provide a pedicle screw and coupling element assembly which provides a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a pedicle screw and rod coupling mechanism having a polyaxially rotating screw head which is selectively lockable at a desired fixed position once a cross bar rod coupling mechanism is secured to it. More specifically, the present invention comprises, in a first embodiment, a bone screw having a semi-spherical head. The shaft of the screw is threaded for insertion, and secure retention in vertebral bone. The ballshaped head has a constant radius of curvature over the curvate portion thereof, which forms a ball top end of the screw. Onto the ball head of the screw is received a cross bar mounting element, which is initially polyaxially disposed on the ball head.

In more detail, the cross-bar mounting element comprises a U-shaped member having a pair of upright extending elements, defining therebetween a trough, and a lower socket portion. With respect to the front and rear faces of the extending members, however, a set of radially extending ridges are disposed on the surface, therein providing a splined conformation. With respect to the socket portion, the cross bar mounting element receives the ball head of the screw into the socket; the socket having substantially the same interior volume as necessary to permit the ball to loosely rotate in the socket. The socket is further provided with a pair of opposing slots which render the socket compressible (the deflection of the slots in a narrowing direction causing a decrease in the total volume of the socket, permitting the crush locking of the ball in the socket. The means by which the slots are deflected and the socket volume reduced is described more fully hereinbelow). In a first embodiment, the pair of slots in fact comprise a single transverse split in the cross bar mounting element, beginning at the bottom (the lower entrance into the socket) and extending up beyond the socket, to a level beyond the bottom of the trough defined by the upwardly extending members (the split laterally dividing the lower portions of the upwardly extending members). In a second, alternative embodiment, the pair of slots extend down from the top of the cross bar mounting element to a point below the maximum radius of the socket. In either embodiment, the application of a compressive force, applied against the opposing faces of the upwardly extending members can, therefore, cause the slots to narrow, and the socket to be compressed.

The cross bar member of the present invention may be substantially similar to the cross bar element of the TSRH™, as described more fully in the Background of the Invention. Alternatively, it shall be understood that any element which can securely retain a rod, and can apply a compressive force against the opposing faces of the cross bar mounting element, is sufficient.

The assembly and implantation of the present invention is set forth hereinbelow. The surgeon prepares the pedicle site for receiving the shaft of the screw. Once the screw is implanted, the cross bar mounting element is mounted to the ball head of the screw. At this point, the cross bar mounting element remains rotationally free to angulate relative to the screw.

Given the cross bar element of the TSRH™, the next step in the implantation process involves positioning the cross bar element along the rod, and placing the threaded first end in the trough of the cross bar mounting element. The polyaxial freedom of the cross bar mounting element permits substantially greater ease of use as the surgeon places the cross bar element in the trough. Finally the surgeon tightens the cross bar element to the cross bar mounting element, thus applying a compressive force to opposing faces of the upwardly extending members. This compressive force causes the pair of slots to compressibly narrow, in turn causing the interior surface of the socket portion of the cross bar mounting element to collapse onto the exterior surface of the ball head of the screw, thus causing the cross bar mounting element and the screw to be locked in position (at the selected polyaxial angle).

Multiple screw assemblies are generally necessary to complete the full array of anchoring sites for the rod immobilization system, however, the screw and coupling element assembly of the present invention is designed to be compatible with alternative rod systems so that, where necessary, the present invention may be employed to rectify the failures of other systems, including the TSRH™, the implantation of which may have already begun.

BRIEF DESCRIPTION OF THE FIGURES

FIG. 1 is a top view of a human vertebra, which is representative of the type for which the present invention is useful for coupling thereto a rod apparatus;

FIG. 2 is a side view of a pair of adjacent vertebrae of the type shown in FIG. 1;

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 5:
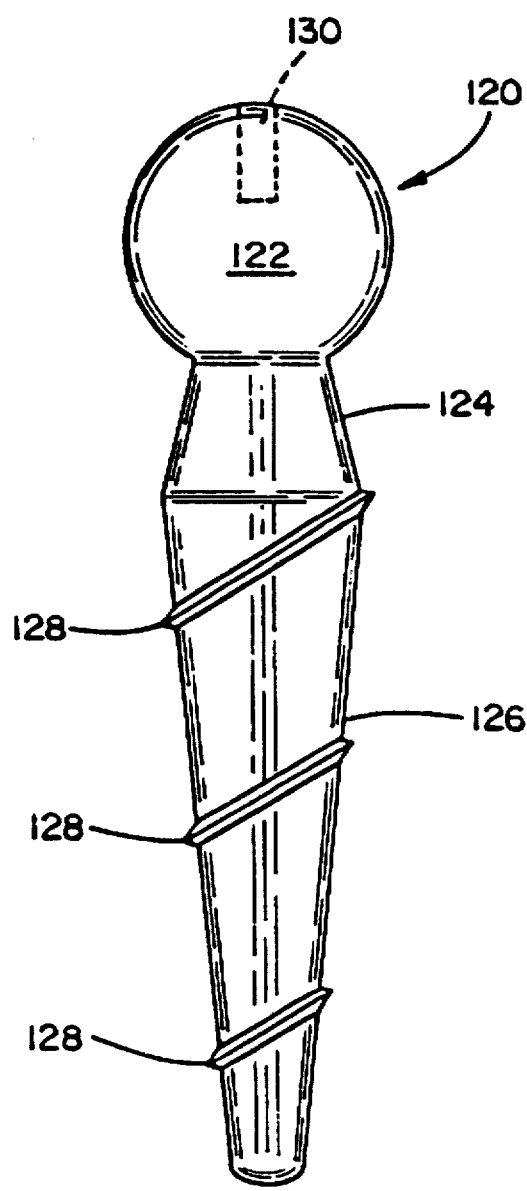
FIG. 5 is a side view of a bone screw having a curvate head which is an aspect of the present invention.

Referring now to FIG. 5, a side view of the screw portion of the present invention, comprising a curvate head, is shown. The screw 120 comprises a head portion 122, a neck 124, and a shaft 126. In FIG. 5, the shaft 126 is shown as having a tapered shape with a high pitch thread 128. It shall be understood that a variety of shaft designs are interchangeable with the present design. The specific choice of shaft features, such as thread pitch, shaft diameter to thread diameter ratio, and overall shaft shape, should be made be the physician with respect to the conditions of the individual patient's bone, however, this invention is compatible with a wide variety of shaft designs.

The head portion 122 of the screw 120 comprises a semi-spherical shape, which has a recess 130 in it. It is understood that the semi-spherical shape is a section of a sphere, in the embodiment shown the section is greater in extent than a hemisphere, and it correspondingly exhibits an external contour which is equidistant from a center point of the head. In a preferred embodiment, the major cross-section of the semi-spherical head 122 (as shown in the two dimensional illustration of FIG. 5) includes at least 270 degrees of a circle.

The recess 130 defines a receiving locus for the application of a torque for driving the screw 120 into the bone. The specific shape of the recess 122 may be chosen to cooperate with any suitable screw-driving tool. For example, the recess 130 may comprise a slot for a screwdriver, a hexagonally shaped hole for receiving an allen wrench, or most preferably, a threading for a correspondingly threaded post. It is further preferable that the recess 130 be co-axial with the general elongate axis of the screw 120, and most particularly with respect to the shaft 126. Having the axes of the recess 130 and the shaft 126 co-linear facilitates step of inserting the screw 120 into the bone.

The semi-spherical head portion 122 is connected to the shaft 126 at a neck portion 124. While it is preferable that the diameter of the shaft 126 be less than the diameter of the semi-spherical head 122, it is also preferable that the neck 124 of the screw 120 be narrower than the widest portion of the shaft 126. This preferable dimension permits the screw to swing through a variety of angles while still being securely held in the socket of the cross bar mounting member (as set forth more fully with respect to FIGS. 6–9).

Figure 6:
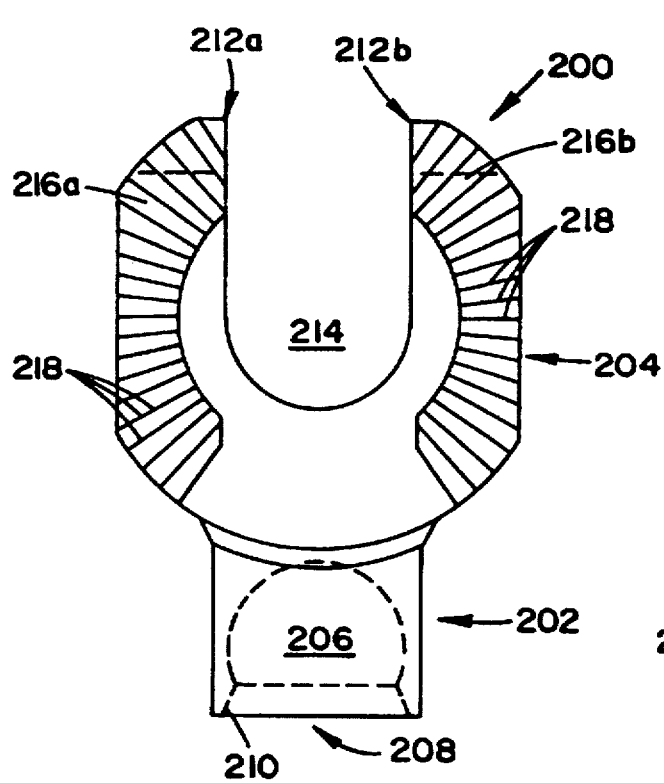
FIG. 6 is a side view of the coupling element of the present invention, wherein critical interior features of the element are shown in phantom.
Figure 7:
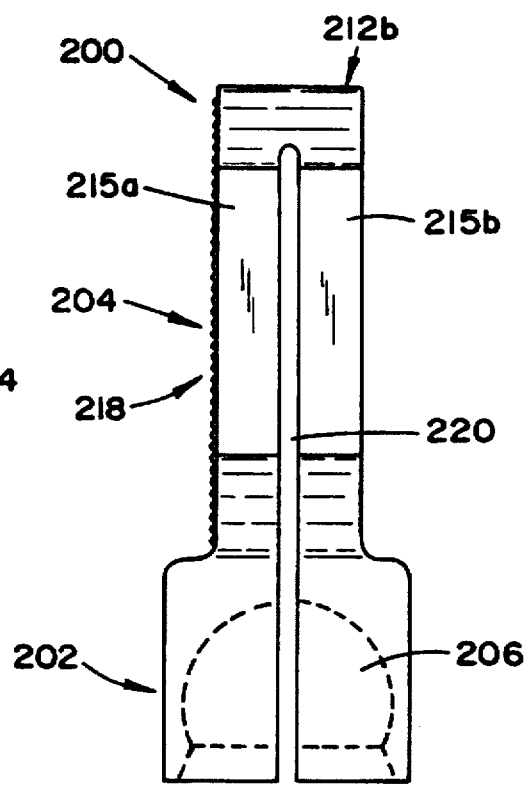
FIG. 7 is another side view of the coupling element of the present invention, taken from a point of view which is rotated 90 degrees from that of FIG. 6, and wherein interior features of the element are shown in phantom.
Figure 8:
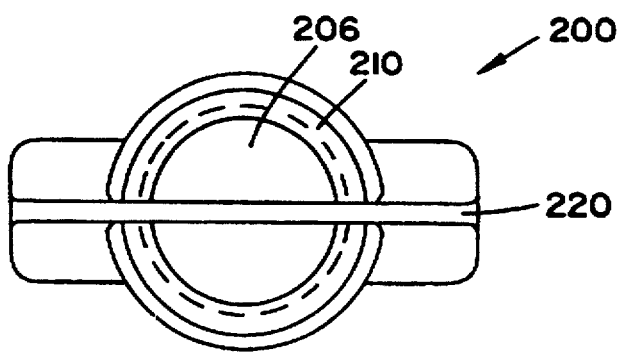
FIG. 8 is a third view of the coupling element of the present invention, taken from from the bottom of the element.

Referring now to FIGS. 6–8, a first embodiment of the cross bar mounting element 200 of the present invention is provided in front side, lateral side, and bottom views, respectively. More specifically with respect to the front side view shown in FIG. 6, the element 200 may be conceptually separated into a lower socket portion 202 and an upper cross bar receiving portion 204. The lower socket portion 202 comprises a cylindrical base having a semi-spherical interior volume 206 provided therein. This interior volume 206 is accessible from the exterior through a bottom opening 208. The ball head 122 of the screw 120 is insertable into the socket 206, and is initially polyaxially rotatable within the socket through a wide range of angles which are limited only by the contact of the neck 124 of the screw against the lip 210 of the opening 208 (the diameter of the neck 124 necessarily being less than that of the opening 208).

The upper portion 204 of the cross bar mounting element 200 comprises a pair of upwardly extending members 212a, 212b which define therebetween a U-shaped trough 214. The front face of the upper portion 204 (the front faces 212a, 216b of the upwardly extending members 212a,212b) includes a series of radially extending ridges 218, which provide a splined conformation thereon.

Referring now also to FIGS. 7 and 8, lateral side and bottom views of the cross bar mounting element 200 are provided. The lower socket portion 202, which includes the interior socket volume 206 necessarily includes a means by which the socket opening 208 may be expanded. This means comprises a vertical split, or slot, 220 which extends upwardly from the bottom of the element 200, into the upper portion. More specifically, the split 220 provides opposing slots on either side of the interior volume 206, and divides the upwardly extending members into front and rear portions (215a and 215b, respectively, of upwardly extending member 212b is shown in this lateral side view). The slot 220 terminates at a point below the ultimate top of the upwardly extending members 212a,212b, such that the cross bar mounting element 200 comprises a single piece. The ball head 122 of the screw 120 may be inserted into the socket 206 when the split 220 is widened by the application of an outward tensile force directed on the front and/or back surfaces of the cross bar mounting element 200. Correspondingly, the application of an inwardly directed compressive force onto the front and back surfaces of the element 200 causes the slot 200 to narrow, thus causing the interior volume 206 to contract. This contraction causes the surface of the interior volume 206 to crush lock to the surface of the ball head 122.

Figures 9, 10:
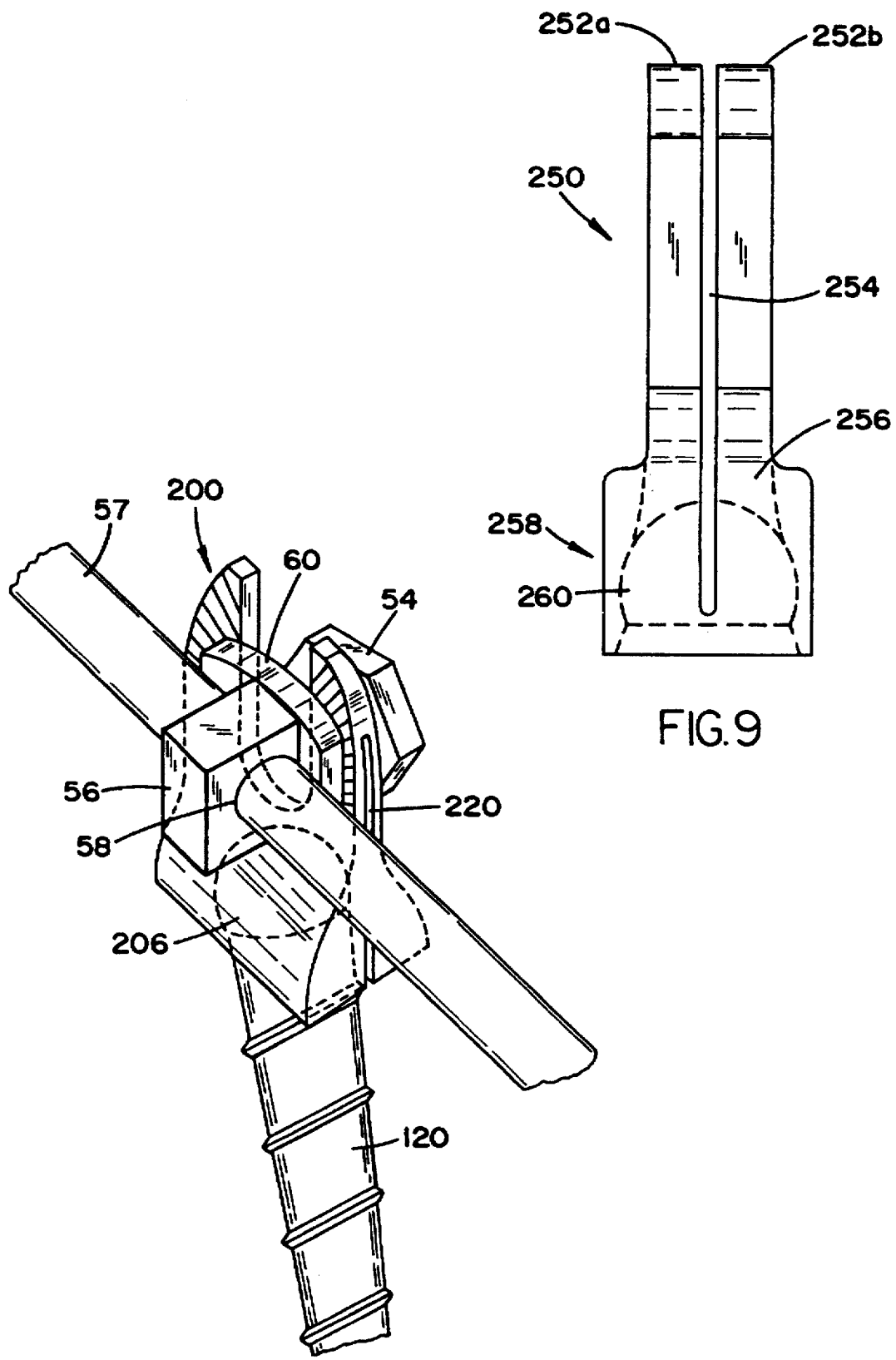
FIG. 9 is a side view of an alternative coupling element of the present invention, taken from the parallel perspective as FIG. 7.
FIG. 10 is a side perspective view of a fully assembled embodiment of the present invention comprising elements shown in FIGS. 4b, 5, and 6 (and 7–8).

Referring now to FIG. 9, an alternative embodiment of the cross bar mounting element 250 is provided in a lateral side view. This alternative embodiment is substantially similar to the cross bar mounting element 200, illustrated in FIGS. 6–8, differeing in the following respects. First, the slot 254 extends from the top of the element 252, down the upwardly extending members (shown here as dividing the element into a front face portion 252a, and a rear face portion 252b) to a position in the lower socket portion 258 which is below the maximum diameter of the socket 260. In order to load the screw 120, this embodiment must also include an opening 256 in the top of the lower socket portion 258. It shall be further understood that an outwardly directed tensile force, applied to the front and rear faces of the element, is required to permit the socket 260 to receive the the head 122 of the screw 120. Further, the application of a compressive force against the front and rear faces of the element 250 causes the socket 260 to contract as before, which locks the head of the screw in the socket. The cross bar member itself, which may comprise a variety of embodiments, is contemplated to provide a rod receiving and securing portion, and a bar portion which seats in the trough 214 of the mounting element 200 or 250 and provides a compressive force against the front and rear surfaces thereof to lock the ball head 122 of the screw 120 therein.

Figure 3:
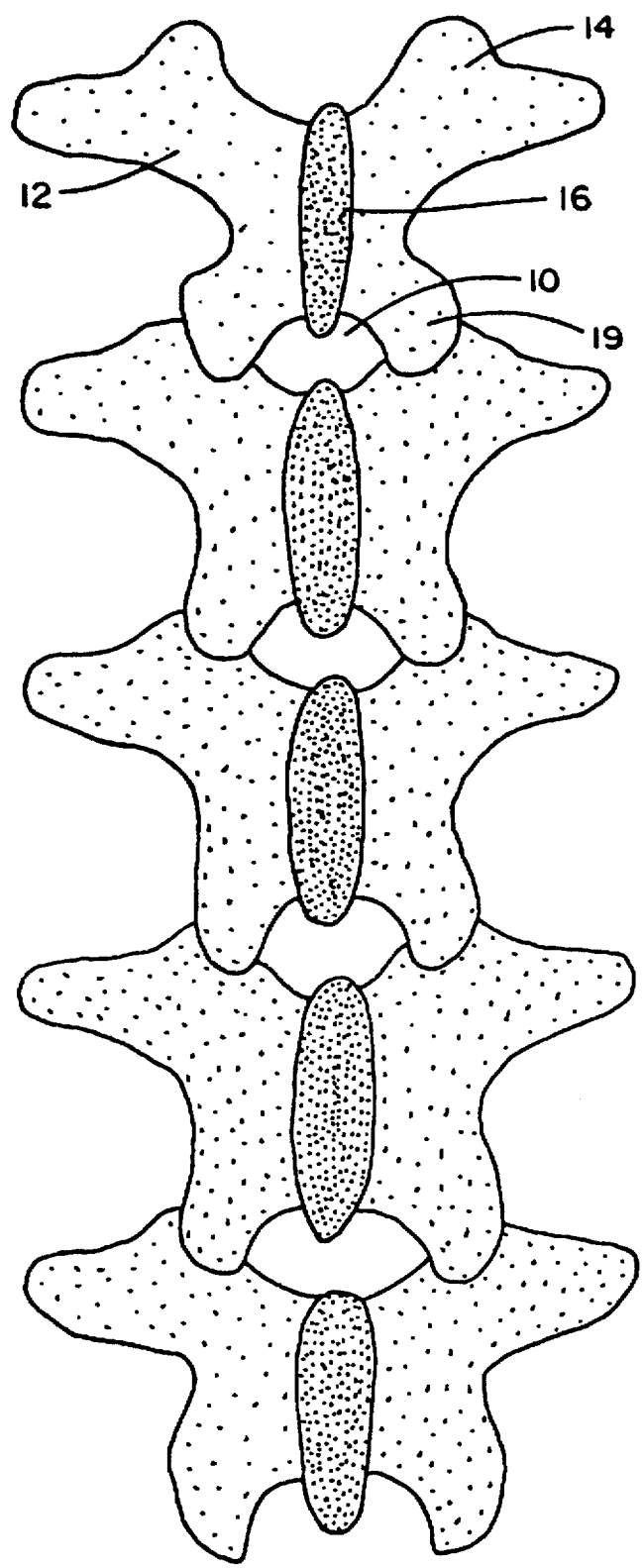
FIG. 3 is a posterior view of a sequence of vertebrae of the type shown in FIGS. 1 and 2.
Figure 4A:
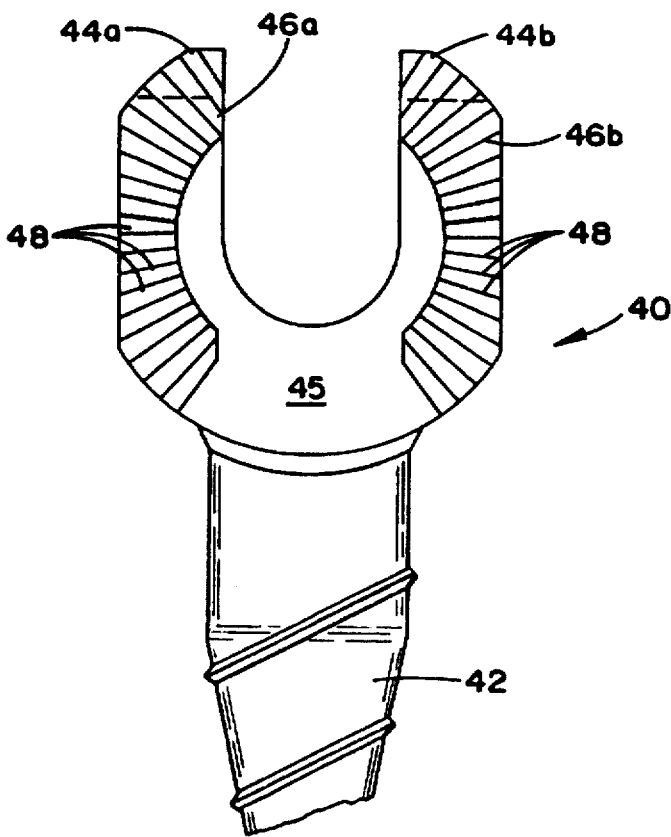
FIGS. 4a and 4b are side views of the TSRH™ screw and rod coupling mechanism of the prior art.
Figure 4B:
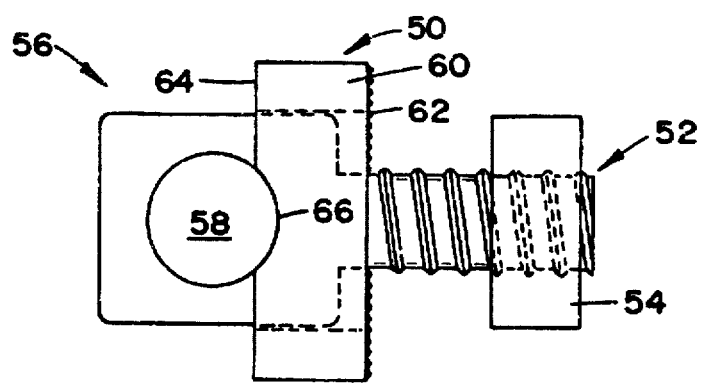

More particularly, with respect to the fully assembled embodiment illustrated in FIG. 10, in a perspective view, the cross bar and the method of assembly of the entire system is described. First, the rod receiving cross bar member 50, as originally shown in FIG. 4b, comprises a first end 52 which is threaded (hidden in FIG. 10), onto which a nut 54 may be advanced. The second end 56 of the cross bar member 50 comprises a hole 58 through which a rod 57 may be disposed. The diameter of the first end 52 is less than the diameter of the second end 56. An annular member 60 is slideably mounted about the middle of the cross-bar member 50 (at the junction of the first and second ends) which has opposing faces 62 and 64. The first face 62, which addresses the first end 52, has a splined conformation, such that it may join with the splined front face of the upper section 204 of the cross bar mounting element 200 (the splining permits a rotational variety of interfacing angles). The second face 64 includes a groove 66 in which the rod 57 may nest when it is positioned through the hole 58. When the first end 42 of the cross bar member 50 is positioned in the U-shaped trough 214, and the nut 54 is advanced, the first face of the disc 60 locks to the spline 218 of the cross bar mounting element 200. Continued advancement of the nut 56 along the threading provides the compressive force (the annulus 60 and the nut 56 together) against the front and rear faces of the cross bar mounting element 200, thereby locking the element 200 to the screw by virtue of the compressed slot and volume 206. Once the compressive force of the annulus 60 and the nut 56 causes the slot 220 to narrow and the head of the screw 120 to be locked in the socket 206, the annulus 60 itself is then slideably pushed toward the second end 56 of the cross-bar member 50 until the second face 64 of the annulus, and more particularly the groove 66, compresses the rod 57 in the hole 58 of the cross bar member 50. This tightening of the nut 54, therefore, locks the assembly together.

While there has been described and illustrated embodiments of a polyaxial screw and coupling element assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A polyaxial screw assembly for use with orthopedic rod implantation apparatus, comprising:

a screw having a curvate head;

a cross bar mounting element having upper and lower portions, said lower portion including an interior socket, said interior socket being capable of polyaxially receiving therein said curvate head, and said upper portion including a pair of upwardly extending members defining therebetween a trough, said cross bar mounting element further including at least one vertical slot extending from said lower portion and into said pair of upwardly extending members of said upper portion, said at least one slot rendering said interior socket contractible by the application of a compression force applied to said at least one slot which causes said at least one slot to narrow; and a cross bar assembly having a first end, a second end, an elongate medial portion, and an annular member positioned about said elongate medial portion adjacent to said first end, said annular member having a diameter which is greater than a separation between the upwardly extending members of the cross bar mounting element, said elongate medial portion being positionable in said trough of said cross bar mounting element such that said annular member contacts a front face of said upper portion of said cross bar mounting element, said first end including means for securely coupling to a rod; and a selectively advanceable means, which is selectively advanceable along said cross bar assembly, from said second end toward said first end, said selectively means having a diameter which is greater than the separation between the upwardly extending members of the cross bar mounting element and which selective advancement into contact with a rear face of said cross bar mounting element applies a compressive force to said cross bar mounting element which in turn causes the at least one slot to narrow and the interior socket to be compressed and thereby compression lock to the curvate head of the screw, securing the screw in the selected position relative to the cross bar mounting element.

2. The assembly as set forth in claim 1, wherein the at least one slot extends vertically from a position beneath a top of the upwardly extending members downward fully through the lower socket portion.

3. The assembly as set forth in claim 1, wherein the at least one slot extends vertically from a position above a bottom of the lower socket portion upward fully through the upwardly extending members.

4. The assembly as set forth in claim 1, wherein said front face of said cross bar mounting element on said upwardly extending members includes a spline.

5. The assembly as set forth in claim 4, wherein the portion of the annular member which contacts the front face of said cross bar mounting element includes a corresponding spline.

6. A orthopedic rod implantation apparatus, comprising:

at least one elongate rod;

a plurality of polyaxial screw assemblies, wherein at least one of said polyaxial screw assemblies includes a screw having a curvate head;

a cross bar mounting element having upper and lower portions, said lower portion including an interior socket, said interior socket being capable of polyaxially receiving therein said curvate head, and said upper portion including a pair of upwardly extending members defining therebetween a trough, said cross bar mounting element further including at least one vertical slot extending from said lower portion and into said upwardly extending members of said upper portion, said at least one slot rendering said interior socket contractible by the application of a compression force applied to said at least one slot which causes said at least one slot to narrow; and a cross bar assembly having a first end, a second end, an elongate medial portion, and an annular member positioned about said elongate medial portion adjacent to said first end, said annular member having a diameter which is greater than a separation between the upwardly extending members of the cross bar mounting element, said elongate medial portion being positionable in said trough of said cross bar mounting element such that said annular member contacts a front face of said upper portion of said cross bar mounting element, said first end including means for securely coupling to a rod; and a selectively advanceable means, which is selectively advanceable along said cross bar assembly, from said second end toward said first end, said selectively advanceable means having a diameter which is greater than the separation between the upwardly extending members of the cross bar mounting element and which selective advancement into contact with a rear face of said cross bar mounting element applies a compressive force to said cross bar mounting element which in turn causes the at least one slot to narrow and the interior socket to be compressed and thereby compression lock to the curvate head of the screw, securing the screw in the selected position relative to the cross bar mounting element.

7. The assembly as set forth in claim 6, wherein the at least one slot extends vertically from a position beneath a top of the upwardly extending members downward fully through the lower socket portion.

8. The assembly as set forth in claim 6, wherein the at least one slot extends vertically from a position above a bottom of the lower socket portion upward fully through the upwardly extending members.

9. The assembly as set forth in claim 6, wherein said front face of said cross bar mounting element on said upwardly extending members includes a spline.

10. The assembly as set forth in claim 9, wherein the portion of the annular member which contacts the front face of said cross bar mounting element includes a corresponding spline.

11. A polyaxial screw assembly for use with orthopedic rod implantation apparatus, comprising:

a screw having a semi-spherical head;

a cross bar mounting element having upper and lower portions, said lower portion including an interior socket, said interior socket being capable of polyaxially receiving therein said semi-spherical head, and said upper portion including a pair of upwardly extending members defining therebetween a trough and a spline on at least one set of exterior faces, said cross bar mounting element further including a pair of opposing vertical slots extending from a point below a top of said upwardly extending members downward fully through said lower portion, said pair of slots rendering said interior socket contractible by the application of a compression force applied to said slots which causes said slots to narrow; and a cross bar assembly having a first end, a second end, a threaded elongate medial portion, and an annular member having a correspondingly splined lateral face directed toward said second end, said annular member being positioned about said elongate medial portion adjacent to said first end, said annular member having a diameter which is greater than a separation between the upwardly extending members of the cross bar mounting element, said elongate medial portion being positionable in said trough of said cross bar mounting element such that said spline face of said annular member contacts said splined face of said upper portion of said cross bar mounting element, said first end including means for securely coupling to a rod; and a nut which is selectively advanceable along said threaded medial portion of said cross bar assembly, said nut having a diameter which is greater than the separation between the upwardly extending members of the cross bar mounting element and which selective advancement into contact with a rear face of said cross bar mounting element applies a compressive force to said cross bar mounting element which in turn causes the at least one slot to narrow and the interior socket to be compressed and thereby compression lock to the semi-spherical head of the screw, securing the screw in the selected position relative to the cross bar mounting element.

* * * * *